CHRYSANTHEMUM PLANT
Filed Oct. 10, 1973
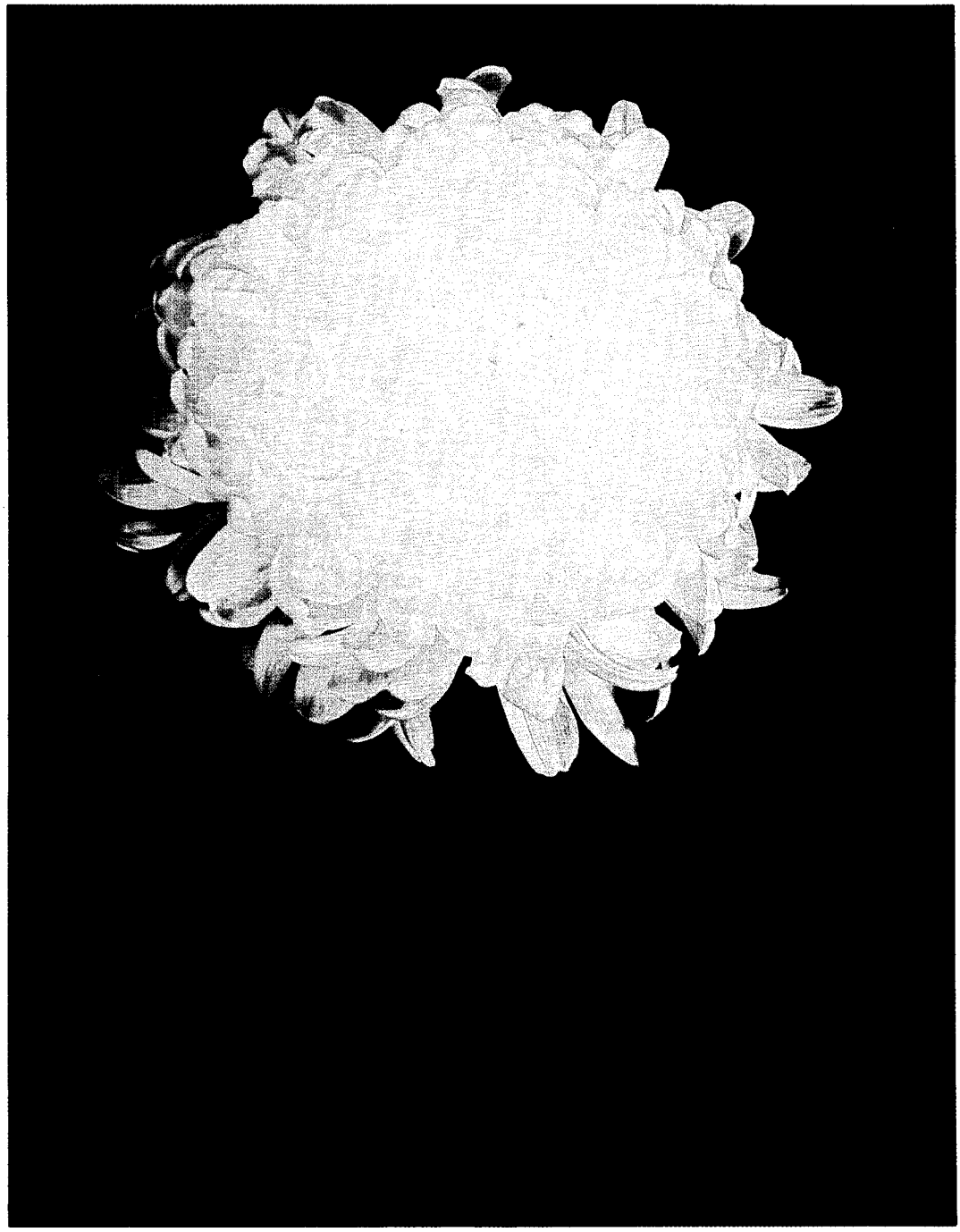

United States Patent Office

Plant Pat. 3,656
Patented Nov. 26, 1974

3,656
CHRYSANTHEMUM PLANT

Walter H. Jessel, Jr., Doylestown, and William E. Duffett, Akron, Ohio, assignors to Yoder Brothers, Inc., Barberton, Ohio Filed Oct. 10, 1973, Ser. No. 404,983
Int. Cl. A01h 5/00
U.S. Cl. Plt.—77 1 Claim The present invention comprises a new and distinct cultivar of chrysanthemum plant known by the varietal name Sea Foam, which is a seedling of #63820–2 × #A138. Both parents are unpatented and identified for breeding purposes by the above breeding numbers.

The new cultivar is categorized as a white winter standard of the same general class as the well-known, unpatented cultvars Improved Mefo and May Shoesmith. However, the new cultivar differs from these cultivars in many important respects, with the primary characteristics of the new cultivar being as follows:

1. A flower size ranging from 5¾" to 6¼" when fully expanded, which is somewhat larger than Improved Mefo but somewhat smaller than May Shoesmith.
2. A relatively early response of approximately nine weeks.
3. A less incurved flower form.
4. Superior form retention.
5. Large and light green foliage with less pronounced marginal indentation.
6. A strong, heavy stem in all seasons.
7. A tolerance of marginal temperatures for uniform bud initiation and development down to 56° F. At lower temperatures, for example, 54° F., Sea Foam will not initiate and flower uniformly.
8. An ivory white flower color.
9. A vigorous growth habit.

The new cultivar was selected from the progeny of the designated cross and when asexually reproduced by cuttings at Barberton, Ohio has been found to retain its distinctive characteristics through successive propagations.

The new cultivar, when grown in the vicinity of Barberton, Ohio has a response period of approximately 9 weeks, and the following detailed description is based on observations made of the new cultivar in a greenhouse in Barberton, Ohio. The response time, blooming period, color, and total vigor may vary significantly with varying environmental conditions such as temperature, daylength, and light intensity. Suggested flowering in the northern and western United States is from October through May; southeastern and southwestern United States is from November through mid-April; coastal California, November through mid-April, and Florida, December through March 15.

The accompanying photographic drawing shows the unique characteristics of the new cultivar, with the color being as nearly true as possible with color illustrations of this type.

In the description which follows, color references are made in the Munsell Color Notation.

Botanical Classification: Chrysanthemum morifolium.

Sea Foam

Bloom:
- *Size.*—5¾".
- *Fully expanded.*—6¼",
- *Borne.*—singly on disbudded plants.
- *Stems.*—strong and heavy.
- *Form.*—semi-incurve.
- *Permanence.*—10–14 days.
- *Color.*—center of flower—pale yellow, 10Y9/4; base of petals—light yellow-green, 2.5GY7/8; inside of petals—light yellow-green, 3.7GY9.1/2.2 to light ivory 10Y9/1; reverse of petals—light ivory, 10Y9/1 to white, N9/; tonality from a distance—ivory white; discoloration—light ivory, 10Y9/1.

Petals:
- *Texture.*—smooth.
- *Appearance and form.*—closed at base, opening slowly with pronounced inward roll along margins. Smooth rounded keel, tapering to a blunt semi-hooded tip.
- *Arrangement.*—composite, whorled on a single receptacle.
- *Persistence.*—resists shatter.
- *Fragrance.*—typical chrysanthemum.

Reproductive Organs:
- *Stamen, anthers.*—5–20.
- *Pollen.*—scant.
- *Arrangement.*—clustered in center of flower, if present.
- *Styles.*—present both ray and disc florets.
- *Length.*—short.
- *Ovaries.*—at the base of petal attached to receptacle.

Plant:
- *Form.*—herbaceous.
- *Growth.*—upright.
- *Height.*—approximately 38–43" given 2–5 long day weeks, and 11–14 weeks total crop time as defined in the timetables of Yoder Brothers, Inc., Barberton, Ohio for the various seasons
- *Spread.*—none grown single stem to slight when pinched.

Foliage:
- *Top side.*—dark green, 7.5GY3/4.
- *Size.*—length to width ratio 31:22 with length to 7¾" and width to 5½".
- *Quantity.*—numerous.
- *Shape.*—spatulate lobed.
- *Texture.*—smooth.
- *Ribs & veins.*—moderately prominent.
- *Edge.*—moderately indented.
- *Serration.*—coarse.
- *Under side.*—greyed medium green, 7.5GY5/4.
- *Stipules.*—very prominent.

We claim:

1. A new and distinct cultivar of chrysanthemum characterized particularly as to its uniqueness by its 5¾"–6¼" flower size, early response of approximately nine weeks, less incurved flower form, superior form retention, large, light green foliage with less pronounced marginal indentation, strong, heavy stems in all seasons, an ivory white flower color, and by its tolerance of marginal temperatures for uniform bud initiation and development.

No references cited.

ROBERT E. BAGWILL, Primary Examiner